United States Patent [19]

Koh et al.

[11] 3,958,957
[45] May 25, 1976

[54] METHANE PRODUCTION

[75] Inventors: Kwang K. Koh, Seabrook; Robert E. Pennington, Baytown; Lonnie W. Vernon, Baytown; Nicholas C. Nahas, Baytown, all of Tex.

[73] Assignee: Exxon Research and Engineering Company, Linden, N.J.

[22] Filed: July 1, 1974

[21] Appl. No.: 485,041

[52] U.S. Cl. .............................. 48/197 R; 252/443; 252/447; 260/449 M; 423/414
[51] Int. Cl.² ........................................... C07C 9/04
[58] Field of Search ..................... 48/197 R, 214; 260/449 M

[56] References Cited
UNITED STATES PATENTS

| | | | |
|---|---|---|---|
| 3,511,624 | 5/1970 | Humphries et al. | 48/197 R |
| 3,759,679 | 9/1973 | Franz et al. | 48/197 R X |
| 3,838,993 | 10/1974 | Aldridge | 48/214 A |
| 3,838,994 | 10/1974 | Aldridge | 48/214 A X |
| 3,842,113 | 10/1974 | Ichikawa et al. | 260/449 M X |
| 3,842,121 | 10/1974 | Ichikawa et al. | 260/449 M X |

Primary Examiner—Joseph Scovronek
Attorney, Agent, or Firm—James E. Reed

[57] ABSTRACT

Methane is produced by contacting a mixture of carbon monoxide or carbon dioxide and hydrogen with a carbon-alkali metal catalyst at a temperature in the range between about 800°F. and about 1500°F. and at a pressure between about atmospheric and about 2000 psig. The catalyst employed may be prepared by heating an intimate mixture of coal, coal char, coke or other carbonaceous solids and an alkali metal salt, hydroxide or similar constituent. Such a catalyst promotes the methanation of carbon monoxide and carbon dioxide and the formation of higher hydrocarbons by the Fischer-Tropsch reaction and at the same time is resistant to high temperature sintering and poisoning by sulfur compounds present in the feed gas. The catalyst can be regenerated if necessary by air oxidation.

18 Claims, 12 Drawing Figures fig.1 fig.2 fig.3 fig.4 fig.5 fig.6 fig.7 fig.8 fig.9 fig.10 fig.11 fig.12

METHANE PRODUCTION

BACKGROUND OF THE INVENTION

1. Field of the Invention:

This invention relates to the manufacture of synthetic fuels and is particularly concerned with a method for the production of methane from synthesis gas and similar mixtures of carbon monoxide or carbon dioxide and hydrogen.

2. Description of the Prior Art:

Conventional processes for the manufacture of synthetic fuels by the gasification of coal or other carbonaceous solids generally require the reaction of steam with carbon at temperatures between about 1200° and about 2500° F. to produce a gas containing hydrogen and carbon monoxide and the subsequent reaction of a portion of the carbon monoxide with steam at lower temperatures to produce carbon dioxide and additional hydrogen by means of the water-gas shift reaction. Following this, the gas is usually treated to remove carbon dioxide and sulfur compounds and then fed to a catalytic methanation unit for reaction of the carbon monoxide and hydrogen to produce methane and water vapor.

The water-gas shift reaction is an important part of processes of the type referred to above because of the need for a high hydrogen concentration in the methanation step. This reaction is equilibrium limited and must be carried out at relatively low temperatures if the required yields of hydrogen are to be obtained. To facilitate this, catalysts such as copper on zinc oxide and ferric oxide promoted by chromic oxide have been used. More recently, it has been disclosed that alkali metal compounds are effective water-gas shift reaction catalysts at temperatures of from about 400° to 700° F. and are less affected by sulfur compounds than many of the earlier materials. It has also been shown that the alkali metal compounds will catalyze the steam-carbon reaction.

The reaction of carbon monoxide and hydrogen to produce methane is normally carried out in the presence of an iron, nickel or cobalt catalyst. The most effective catalysts have generally been compositions containing nickel as the primary constituent and including small amounts of a promoter such as thorium oxide, magnesium oxide, aluminum oxide, potassium oxide, calcium oxide, potassium carbonate, manganese or the like. The promoters alter the chemical and physical characteristics of the catalyst surface and in low concentrations tend to improve the yield or selectivity obtained with the catalyst. These materials may be employed in conjunction with carriers such as kieselguhr, pumice, infusorial earth, asbestos, silica, alumina or the like. Nickel or alumina containing a small amount of potassium carbonate as a promoter is currently considered by those skilled in the art as the best available methanation catalyst.

Although methanation catalysts of the type referred to above are reasonably effective, experience has shown that such materials are highly sensitive to sulfur compounds and are quickly poisoned. To avoid this, the gases fed to the methanation reactor must be treated to remove both organic and inorganic constituents containing sulfur. This is generally done by first scrubbing the gas stream with a solvent such as methanol to eliminate most of the hydrogen sulfide and mercaptans and then removing the last traces of these impurities by adsorption on reduced zinc oxide or a similar adsorbent. Periodic regeneration of the catalysts by treatment with hydrogen is generally necessary. These feed gas purification and catalyst regeneration steps are expensive.

SUMMARY OF THE INVENTION

The present invention provides an improved process for the production of methane from mixtures of carbon oxides and hydrogen which at least in part avoids the difficulties referred to above. In accordance with the invention, it has now been found that high yields of methane can be obtained by contacting a mixture of carbon monoxide or carbon dioxide and hydrogen with a carbonalkali metal catalyst at a temperature in the range between about 800° F. and about 1500° F. and at a pressure between about atmospheric and about 2000 psig. Experimental work has shown that these catalysts, produced by heating an intimate mixture of coal, coke or similar carbonaceous solids with an alkali metal constituent to an elevated temperature, are surprisingly effective for the methanation of carbon monoxide and carbon dioxide; that they resist poisoning by sulfur compounds in the feed gas stream and therefore require less pretreatment of the gas than conventional iron, nickel and cobalt type catalysts; that, unlike the conventional catalysts, they are resistant to high temperature sintering and catalyst degradation; that they can be readily regenerated by oxidation in air to eliminate any carbon laydown which may occur; and that they are considerably less expensive than the conventional catalysts used and proposed for use in the past. As a result of these and other advantages, methanation processes using these catalysts have many potential applications.

The effectiveness of the carbon-alkali metal catalysts is surprising in view of earlier work on the use of potassium carbonate and similar alkali metal compounds as promoters for iron, nickel and cobalt-type catalysts. Studies have shown that the presence of small amounts of potassium carbonate or the like has a beneficial effect upon the activity and product distribution obtained in high pressure, low temperature carbon monoxide-hydrogen reactions carried out in the presence of iron-type catalysts but that the catalytic activity decreases if the alkali metal compound is present in a concentration in excess of about 1 part per 100 parts of iron. Moreover, it has been shown that the alkali metal compounds catalyze the decomposition of methane, alone or in the presence of steam, to form carbon monoxide and hydrogen. Despite this, it has now been found that the carbon-alkali metal catalysts, substantially free of iron, nickel and cobalt, are highly effective catalysts for the methanation of carbon oxides and that these catalysts have pronounced advantages over the conventional catalysts containing alkali metal compounds as promoters. The reasons for this are not fully understood. There are indications, however, that the alkali metal constituents react with the carbonaceous materials to form alkali metal-carbon interlamellar compounds and that the catalytic effects obtained may be due at least in part to the presence of the reaction products.

The process of the invention can be used for the methanation of synthesis gas produced by the gasification of coal, coke, shale, oil, heavy crude oil, naphtha and similar carbonaceous feedstocks or other mixtures of hydrogen and carbon oxides and may be carried out in a fixed bed, moving bed or fluidized bed system. In a preferred embodiment of the process, raw synthesis gas produced by the gasification of coal in a fluidized bed reactor is methanated in a series of fixed bed reaction vessels at temperatures between about 900° and about 1350° F. and at a pressure between about 100 and about 259 psig. The methanation reaction which occurs is exothermic in nature and hence the gas may be cooled between successive methanation stages. The resulting gas can then be treated for the removal of carbon dioxide, sulfur compounds and other impurities and employed as a fuel of intermediate B.t.u. content or further methanated to produce a high B.t.u. synthetic natural gas.

DESCRIPTION OF THE PREFERRED EMBODIMENTS

Figure 1:
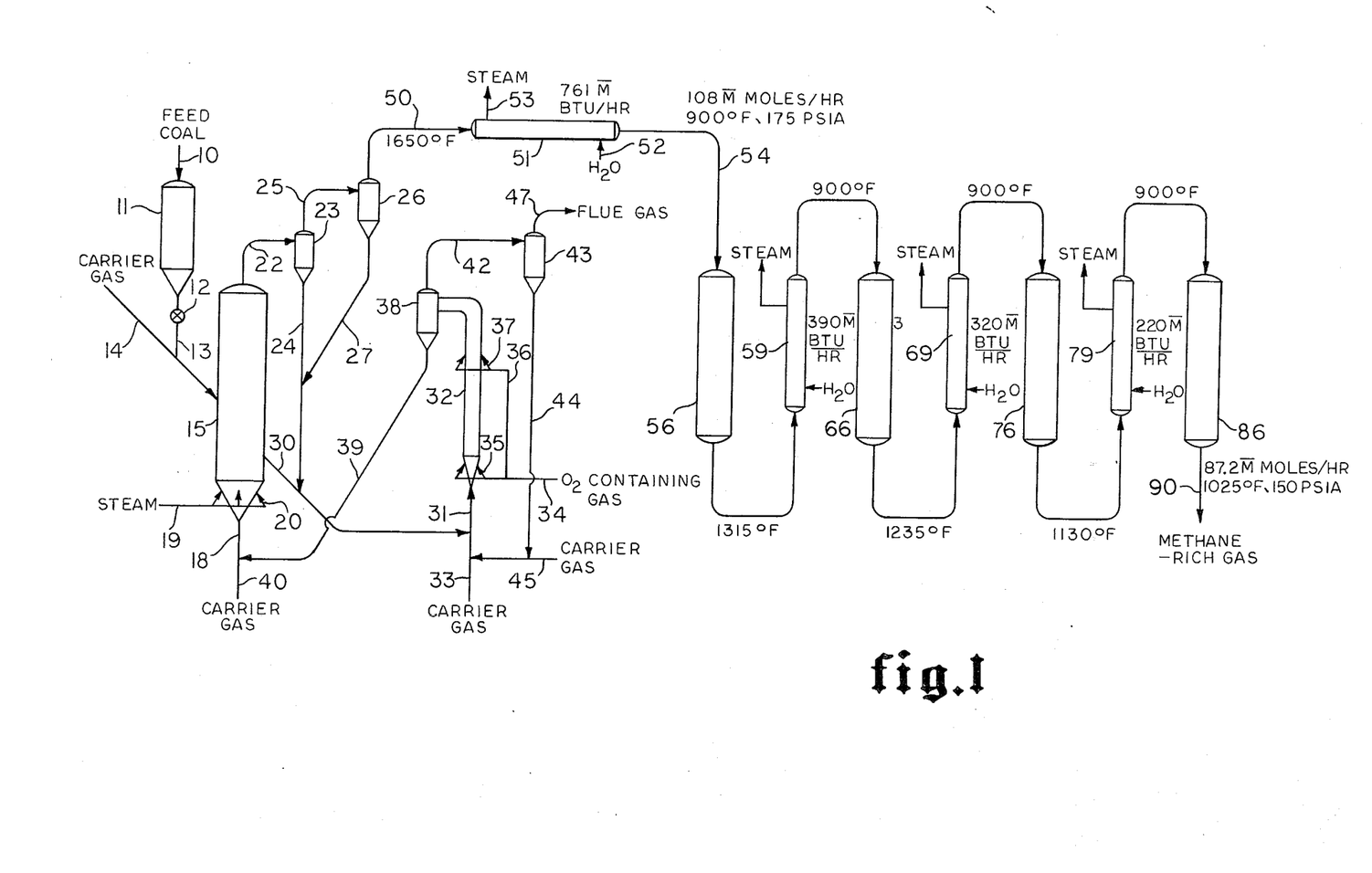
FIG. 1 in the drawing is a schematic flow sheet of a process for the production of a methane-rich gas from coal carried out in accordance with the invention.

FIG. 1 in the drawing is a schematic flow diagram illustrating a process in which a raw synthesis gas produced by the steam gasification of coal is methanated in the presence of a carbon-alkali metal catalyst. It will be understood that the invention is not restricted to the methanation of synthesis gases produced from coal and is equally applicable for the upgrading of synthesis gas and similar mixtures of carbon oxides and hydrogen derived from shale oil, heavy crude oils, petroleum coke, residual petroleum fractions, naphthas and the like.

In the process shown in FIG. 1, a solid carbonaceous feed material, normally bituminous coal, subbituminous coal, lignite or similar material crushed to a particle size of about 8 mesh on the U.S. Sieve Series Scale or smaller is fed into the system through line 10 from a feed preparation plant or storage facility which does not appear in the drawing. The feed material may have been impregnated with a solution of an alkali metal compound in order to catalyze the steam gasification reaction if desired. The coal or other material thus provided is introduced into a closed hopper or similar vessel 11 from which it is discharged through star wheel feeder or an equivalent device 12 in line 13 at an elevated pressure sufficient to permit its introduction into the gasification apparatus at the system operating pressure or a slightly higher pressure. The system of the invention is not restricted to this particular type of an arrangement and parallel lock hoppers, pressurized hoppers, aerated standpipes operated in series or other apparatus may be employed in lieu of or in addition to that shown in order to raise the input coal stream to the required pressure level. The use of such equipment for the handling of coal and other finely divided solids at elevated pressures has been described in the literature and will therefore be familiar to those skilled in the art. Suitable equipment is available commercially.

The coal or other solid feed particles introduced into the system as described above are entrained in carrier gas admitted through line 14 and carried into gasifier 15. The carrier gas stream will normally consist of high pressure steam or product gas. The use of recycled product gas avoids reduction of the hydrogen concentration in the gasifier and is therefore normally preferred. The carrier gas stream is introduced into the system at a pressure between about 50 and about 1500 psig, depending upon the pressure at which gasifier 15 is operated and the solid feed material employed, and is preferably introduced at between about 100 and about 500 psig. The gas is normally preheated to a temperature in excess of about 300° F. but below the initial softening point of the coal or other hydrocarbonaceous feed material. For the gasification of bituminous coals, the use of carrier gas at temperatures in the range between about 400° and about 550° F. is generally preferable. The coal or other feed particles, preferably less than about 20 mesh in size on the U.S. Sieve Series Scale, are suspended in the carrier gas stream in a ratio between about 0.2 and about 2.0 pounds of solid feed material per pound of carrier gas. The optimum ratio for the particular system will depend in part upon the feed particle size and density, the molecular weight of the gas employed, the temperature of the solid feed material and input gas stream, and other factors. In general, ratios between about 0.5 and about 1.5 pounds of coal or other solid feed per pound of carrier gas are preferred.

The feed stream prepared by the entrainment of coal or other solid particles from line 13 in the gas introduced through line 14 is fed into the gasifier through one or more fluid-cooled nozzles not shown in the drawing. The cooling fluid will normally be low pressure steam but may also be water or the like. This fluid may be circulated within the nozzle for cooling purposes or injected into the gasifier around the stream of feed gas and entrained solids to control entry of the solids into the fluidized bed in the gasifier. The number of nozzles employed will depend primarily on the size of the gasifier. Although only one injection line is shown in the drawing, it will generally be preferred to employ a series of nozzles spaced at intervals about the gasifier periphery.

The gasifier employed in the system shown comprises a refractory lined vessel containing a fluidized bed of char particles introduced into the lower portion of the system through bottom inlet line 18. The inlet line extends upwardly through the bottom of the gasifier to a point above a grid or similar distribution device located therein. Steam for maintaining the char particles in a fluidized state and reacting with the char to produce a synthesis gas containing hydrogen and carbon monoxide is introduced into the lower portion of the gasifier below the grid or other distribution device through manifold line 19 and steam injection lines 20. The installation shown employs four steam injection lines spaced at 90° intervals about the periphery of the gasifier but a greater or lesser number may be employed if desired. The steam thus introduced will normally be fed into the system at a rate within the range between about 0.5 and about 2.0 pounds per pound of coal or other solids feed. The upflowing steam and suspended char particles form a fluidized bed which extends upwardly in the gasifier to a level above that at which the coal or other solids feed particles are introduced with the feed gas from line 14. The upper surface of the fluidized bed within the gasifier will normally be located a substantial distance above the feed injection level but sufficiently below the upper end of the gasifier to permit disengagement of the heavier char particles that may otherwise tend to be entrained with the gas leaving the bed.

In the particular gasifier shown in the drawing, the lower portion of the fluidized bed between the grid or other distribution device and the level at which the coal or other solids feed material are introduced into the system serves as a steam gasification zone. Here the steam introduced through the manifold and steam injection lines reacts with carbon in the hot char particles to form synthesis gas containing hydrogen and carbon monoxide. The hydrogen concentration in the gaseous phase of the fluidized bed increases from essentially zero at the bottom of the bed to a value from about 30 to about 50 volume percent near the upper surface of the bed. The temperature in the steam gasification zone will generally range between about 1450 and about 1950° F. Depending upon the particular feed material and particle size employed, the gas velocities in the fluidized bed will generally range between about 0.2 and about 2.0 feet per second or more.

The upper portion of the fluidized bed in gasifier 15 serves as a hydrogasification zone where the feed coal is devolatilized and at least part of the volatile matter thus liberated reacts with hydrogen generated in the steam gasification zone below to produce methane. The level at which the solids feed stream is introduced and hence the location of the steam gasification and hydrogasification zones depend in part upon the properties of the particular coal or other carbonaceous solid which is employed as the feed material for the process. It is generally preferred to select the injection level so that the methane yield from the gasifier will be maximized and the tar yield minimized. In general, the amount of methane produced increases as the coal feed injection point is moved toward the top of the fluidized bed. The tar formed from the input coal or other carbonaceous solids normally also increases as the feed injection point is moved upwardly and decreases as it is moved toward the bottom of the fluidized bed, other operating conditions being the same. The solids feed streams should generally be introduced into the gasifier at a point where the hydrogen concentration in the gas phase is in excess of about 20% by volume, preferably between about 30 and about 50% by volume.

It is normally preferred that the upper level of the fluidized bed be maintained sufficiently above the feed injection level to provide at least about 4 seconds of residence time for the gas phase in contact with the fluidized solids in the hydrogasification zone. A residence time between about 10 and about 20 seconds is normally preferred. The optimum hydrogen concentration at the feed injection point and the gas residence time above that point will vary with different types and grades of coal or other carbonaceous solids and will also change with variations in the gasifier temperature, pressure, steam rate and other process variables. Higher rank bituminous coals normally require somewhat more severe reaction conditions and longer residence times to obtain high methane yields than do coals of lower rank and other carbonaceous solids. Similarly, high reaction temperatures and steam rates generally tend to increase the hydrogen concentration of the gas phase and reduce the solids residence time needed to secure acceptable methane yields from a feed material.

Raw product gas from the fluidized bed moves upwardly from the upper surface of the bed, carrying entrained solids with it. This gas is withdrawn from gasifier 15 through overhead line 22 and passes to a cyclone separator or similar separation device 23 where the larger entrained particles are separated from the gas. The solids thus removed are conveyed downwardly through dipleg 24 for reintroduction into the system as described hereafter. The overhead gas from the separation unit is passed through line 25 to a second separation unit 26 where additional fines are removed. These particles are withdrawn by means of dipleg 27 and may be combined with the particles from diplegs 24 for reintroduction into the gasifier. A preferred procedure, however, is to introduce the fines from diplegs 24 and 27 into a stream of char particles withdrawn from the fluidized bed in gasifier 15 by means of line 30. A dense phase stream of the combined particles are introduced into an upflowing stream of carrier gas in line 31 and carried into transfer line burner 32. The carrier gas may be steam, recycle product gas, flue gas, nitrogen or the like introduced through line 33. The use of recycle flue gas is generally preferred. As the particles move upwardly into the transfer line burner, an oxygen-containing gas, normally air or a mixture of air and flue gas, is introduced into the burner through manifold line 34 and multiple injection nozzles 35 in sufficient quantity to initiate the combustion of carbon and promote a transition from dense phase to dilute phase flow.

The combustion which takes place in the burner results in the generation of flue gas and heating of the unburned particles. It is normally preferred to introduce additional air or other oxygen-containing gas into the transfer line burner at one or more higher points in the burner to secure better control of the combustion process. In the system shown, additional oxygen-containing gas is passed through line 36 and injected into the upper part of the burner through multiple injection nozzles 37. The total quantity of oxygen introduced into the burner should normally be sufficient to permit the combustion of enough carbon to effect a temperature rise in the unburned particles of from about 50° to about 300° F., preferably about 200° F. The total quantity of oxygen needed and the volume of oxygen-containing gas which will be required for a particular set of operating conditions can be readily calculated. In general, it is normally preferred to inject air at the rate from about 0.02 to about 0.2 pound per pound of char being circulated through the burner. The total residence time of the char solids within the burner will normally range between about 0.3 and about 5.0 seconds. The gas velocities needed to achieve such residence times will depend in part on the dimensions of the burner and the solids throughput and can be calculated. Excessively high gas velocities which may produce undue particle attrition should normally be avoided.

The hot flue gas and entrained solids leaving the upper end of transfer line burner 32 are passed to cyclone separator or similar separation device 38 where the larger particles are removed from the gas stream. The separated particles, normally at a temperature of from about 50° to about 300° F. above the fluidized bed temperature, are withdrawn through standpipe 39 and introduced as a dense phase stream into an upflowing stream of carrier gas admitted into gasifier bottom inlet line 18 through carrier gas line 40. The carrier gas may be steam, recycle product gas, flue gas or the like. The use of recycle product gas is normally preferred. The hot solids are entrained in the carrier gas and carried upwardly through line 18 into the fluidized bed above the grid or other distribution device in the lower part of the gasifier. This provides the heat required to maintain the gasification reaction taking place within the gasifier.

The flue gas taken overhead from separation device 38 is passed through line 42 to a second cyclone separator or other separation device 43. Here fine particles not taken out in separation unit 38 are removed from the gas and passed downwardly through standpipe 44. These fines are then entrained in a stream of carrier gas introduced into the system through line 45 and are injected into the upflowing carrier gas admitted through line 32 for reintroduction into the transfer line burner. The fines thus recycled to the burner tend to burn preferentially and improve the carbon utilization in the system. The flue gas taken overhead from separation unit 43 through line 47 may be passed through one or more additional cyclone separators or other devices for the removal of additional entrained fines, passed through a heat recovery system for the recovery of energy from the hot gas, and then scrubbed or otherwise treated to take out sulfur compounds and other contaminants which might otherwise tend to pollute the atmosphere. Following this, the flue gas can be vented to the atmosphere or employed as an inert gas.

The gasification stage of the system shown in FIG. 1 has been described above in terms of a particularly effective gasification process but it should be understood that other gasification procedures may be employed. Depending upon the particular type of gasifier used, the feed materials employed and the operating conditions selected, the temperature of the raw product gas leaving the gasification system may range between about 1200° and about 2500° F. Pressures may vary from between about 30 psig to about 2000 psig or higher. For purposes of describing the methanation process of the invention, it will be assumed that the exit gas withdrawn overhead from separator 26 through line 50 comprises 108 million moles of gas per hour and is at a temperature of 1650° F. and at 175 psia. The composition of this gas stream, excluding sulfur compounds and other contaminants, may be as follows:

TABLE I

| Component | Raw Synthesis Gas Composition Mol % |
|---|---|
| $H_2$ | 36.01 |
| CO | 20.87 |
| $CO_2$ | 10.19 |
| $H_2O$ | 23.30 |
| $CH_4$ | 8.87 |
| $C_2H_6$ | 0.76 |

This gas stream is cooled to the desired methanation temperature by passing it through a heat exchanger or other heat recovery unit 51 where it passes in indirect heat exchange with water or other cooling fluid introduced through line 52 and withdrawn as steam or hot fluid by means of line 33. The cooled gas is withdrawn from the heat recovery unit through line 54 and will normally have a temperature between about 800° and about 1500° F. In the system shown, a temperature of 900° F. will be assumed.

The methanation process of the invention is normally carried out in multiple stages, provisions being made for cooling the gas between successive stages to recover the exothermic heat which is liberated during the methanation process. This generally involves a series of separate reactors with heat exchangers or other heat recovery units interposed between adjacent reaction vessels but in some cases reactors containing two or more methanation stages and intercoolers or similar internal means for removing heat between stages may be employed. The reactors used may be fixed bed, moving bed or fluidized bed units. In the system shown in FIG. 1, four fixed bed reactors designated by reference numerals 56, 66, 76 and 86 and three heat exchangers or similar heat recovery units designated by reference numerals 59, 69 and 79 are provided. The reactors shown are of the downflow type in which the gas moves downwardly through catalyst particles supported on trays or similar internal supporting elements but fixed bed units of other types can also be used.

The catalyst employed in the methanation bed reactors shown in FIG. 1 of the drawing is a carbon-alkali metal catalyst prepared by heating an intimate mixture of carbonaceous solids and an alkali metal constituent to an elevated temperature. Carbonaceous solids which may be employed in preparing the catalyst include coal, coal char, metallurgical coke, petroleum coke, charcoal, activated carbon and the like. The solid particles may range in size from fine powders to coarse lumps, particles between about 4 and about 100 mesh on the U.S. Sieve Series Scale generally being preferred. Any of a variety of alkali metal constituents may be used in combination with these carbonaceous solids. Suitable constituents include the alkali metal carbonates, bicarbonates, formates, biphosphates, oxalates, aluminates, amides, hydroxides, acetates, sulfates, hydrosulfates, tungstates, sulfides and the like. All of these are not equally effective and hence catalysts prepared from certain compounds may give somewhat better results than can be obtained with catalyst prepared from others. In general, cesium, potassium, sodium and lithium salts derived from organic or inorganic acids having ionization constants less than 1 ×

$10^{-3}$ and the alkali metal hydroxides are preferred. The cesium compounds are generally the most effective, followed by the potassium, sodium and lithium compounds in that order. The carbonaceous solids can be combined with the alkali metal constituents to form an intimate mixture of the two by dissolving a water-soluble alkali metal salt or hydroxide in an aqueous carrier, impregnating the solids with the resulting aqueous solution by soaking them in the solution or spraying the solution onto the solids, and drying the treated solids. The dried material is thereafter heated to an elevated temperature, preferably between about 800° and about 1200° F. In some cases, the carbonaceous solids can also be impregnated by suspending a very finely divided alkali metal or compound in a hydrocarbon solvent or inert liquid carrier of low viscosity and thereafter treating the solids with the liquid containing the alkali metal. In other instances, it may be advantageous to pelletize a mixture of very finely-divided alkali metal or compound, carbon and an oil or similar binder and then heat the pellets to an elevated temperature. Other preparation methods may also be used. It is normally preferred to combine the carbonaceous material with from about 5 to about 50% by weight of the alkali metal constituent, preferably at least 10% by weight. If an impregnation process is used, multiple impregnation and drying steps may be employed in order to achieve high alkali metal compound-to-carbon ratios. If desired, the catalysts may be presulfided by exposing them to hydrogen sulfide before they are used.

The mechanisms which take place as a result of impregnating or otherwise combining the carbonaceous solids with alkali metal constituents and heating the treated solids to elevated temperatures are not fully understood but the alkali metals apparently react with the carbon to form carbon-alkali metal compounds or complexes. Studies have shown that neither the carbonaceous solids nor the alkali metal compounds alone are effective methanation catalysts and that high catalytic activity is obtained only when the carbon-alkali metal compounds or complexes are employed. Both constituents of the catalysts are therefore necessary. The resulting catalysts are resistant to degradation in the presence of sulfur compounds and resist sintering at high temperatures. As a result of their high activity, these catalysts have pronounced advantages over methanation catalysts which have been employed in the past.

In the presence of the carbon-alkali metal catalysts, hydrogen and carbon oxides present in the raw synthesis gas fed to the methanation unit react to form methane as indicated by the following equations:

$$2CO + 2H_2 \rightleftarrows CH_4 + CO_2$$

$$CO + 3H_2 \rightleftarrows CH_4 + H_2O$$

$$CO_2 + 4H_2 \rightleftarrows CH_4 + 2H_2O$$

Figure 2:
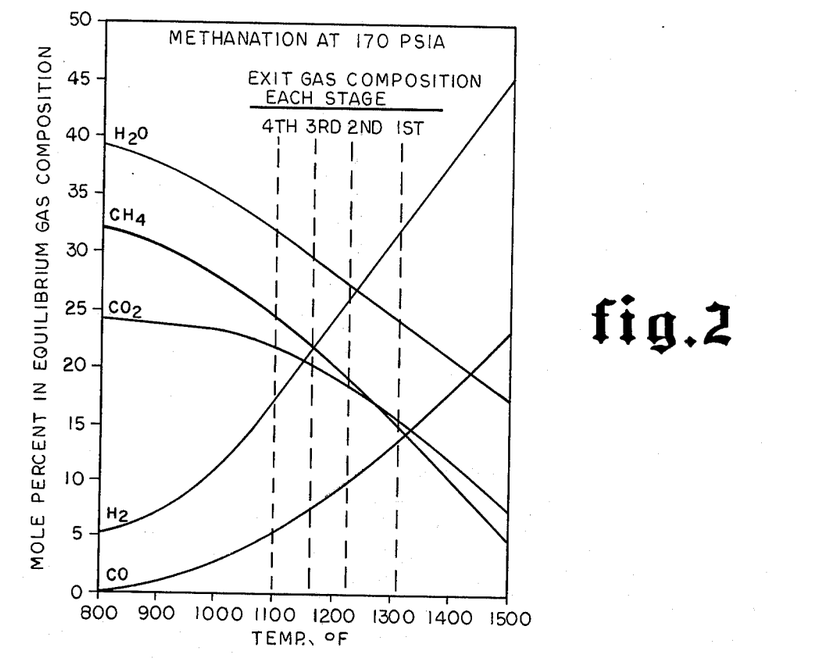
FIG. 2 is an equilibrium diagram showing gas compositions as a function of temperature for the system of FIG.1.

It has been found that the above reactions, as well as other gas phase reactions involving carbon, hydrogen and oxygen which may also take place, are essentially in equilibrium in the presence of the carbon-alkali metal catalysts and that high methane yields can therefore be obtained by proper control of the methanation conditions. This is illustrated by FIG. 2 in the drawing, which is a diagram showing the equilibrium gas composition for a synthesis gas containing hydrogen, carbon monoxide, carbon dioxide, methane and steam in the presence of an alkali metal catalyst at a pressure of 170 psia and at temperatures between 800° and 1500° F. It will be noted that the hydrogen and carbon monoxide contents increase and that the steam, methane and carbon dioxide contents decrease as the temperature is raised. By operating the methanation stages at successively lower temperatures, the methane content of the gas can be increased substantially as the gas passes from one stage to the next. The specific system illustrated in the drawing is designed for the methanation of a gas having an initial methane content of about 8.9 mol percent to produce a gas containing about 24.8 mol percent methane. This is done in four stages operated at gas exit temperatures of 1315° F., 1235° F., 1130° F. and 1025° F., respectively. Following each of the first three stages, the gas is cooled to the initial 900° F. starting temperature in heat exchange units 59, 69 and 79. In each heat exchange unit, the gas is passed in indirect heat exchange with water or other cooling fluid and steam or other hot fluid is recovered.

Figure 3:
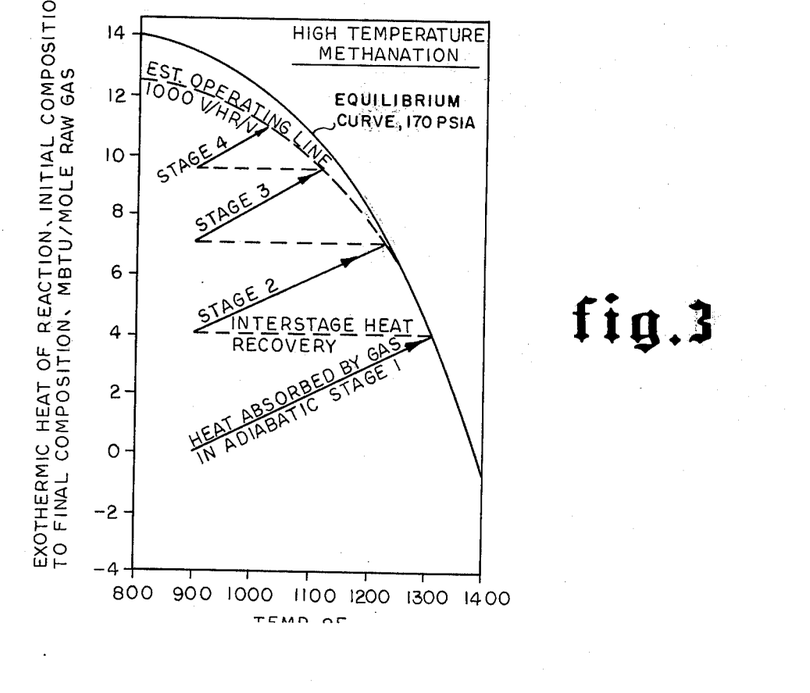
FIG. 3 is a diagram illustrating the heat relationships in the system of FIG. 1.

The thermal characteristics of the specific system illustrated in FIG. 1 are shown in FIG. 3 of the drawing. FIG. 3 is a plot showing the exothermic heat of reaction and temperature as synthesis gas moves through the methanation unit. It will be noted that the operating line for this system is based on a feed rate of 1000 volumes of gas per hour per volume of catalyst and will fall slightly below the equilibrium curve for the system at 170 psia. FIG. 3 shows the exothermic heat of reaciton adsorbed by the gas in each of the stages and the heat recovery which takes place as the gas is cooled from the exit temperature back to the starting temperature of 900° F. It will be understood, of course, that the invention is not restricted to the use of four methanation stages as shown or to the particular operating conditions selected for this system. Instead, the methanation process may be carried out in one or more stages at operating temperatures between about 800° and about 1500° F. and at pressures between about atmospheric and about 2000 psig.

The gas withdrawn from the methanation unit through line 90 has a substantially higher methane content than the raw gas from the gasification stage of the process. In the specific system depicted in FIG. 1, this stream comprises about 87.2 million mols per hour of gas at a temperature of 1025° F. and 150 psia. The composition of the gas, excluding sulfur compounds and other contaminants present in relatively small quantities, is set forth in the following table:

TABLE II

| Component | Mol % |
|---|---|
| $H_2$ | 17.29 |
| CO | 4.59 |
| $CO_2$ | 21.97 |
| $H_2O$ | 31.40 |
| $CH_4$ | 24.76 |

This gas can be cooled to condense the steam and treated by conventional means to remove the acid constituents, primarily carbon dioxide and hydrogen sulfide, in the conventional manner. The resulting product gas will have a heat content in excess of 800 B.t.u.s per SCF and can therefore be used as a fuel without further treatment. If desired, however, the purified gas can be further methanated at lower temperatures to produce a product gas having a B.t.u. content similar to that of natural gas.

The nature and objects of the invention are further illustrated by the results of laboratory work in which carbon-alkali metal catalysts were prepared and employed for the methanation of synthesis gas and mixtures of hydrogen and carbon oxides.

EXAMPLE 1

Figure 4:
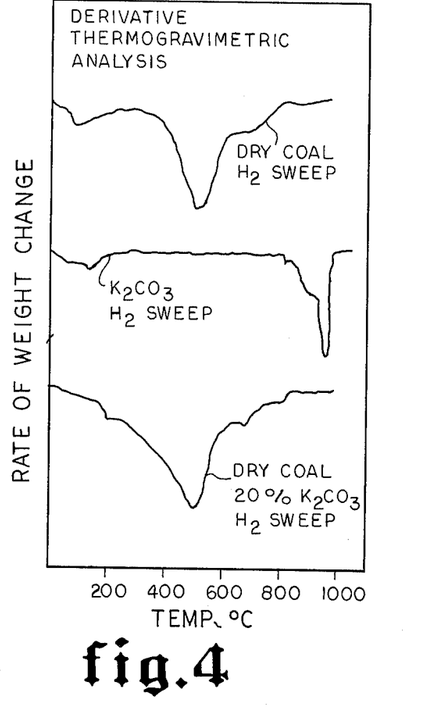
FIG. 4 is a plot showing the results of the derivative thermogravimetric analysis of a catalyst prepared in accordance with the invention.

A carbon-alkali metal catalyst was prepared by drying particles of Wyodak coal at 210° under vacuum and then impregnating the coal particles with an aqueous potassium carbonate solution containing 20 weight percent potassium carbonate based on the coal. The impreganted particles were again dried at 210° F. under vacuum. Following this, the resultant particles were tested in a derivative thermogravimetric analysis apparatus using hydrogen at atmospheric pressure as a sweep gas and a gas flow rate of 0.8 standard cubic feet per hour. The sample was heated in the apparatus at the rate of 50° C. per minute and the loss in weight of the material as the temperature was raised from room temperature to about 1000° C. was recorded. For comparison purposes, dry samples of the Wyodak coal without the potassium carbonate and samples of the potassium carbonate without any coal were tested similarly. The derivative thermogravimetric analysis curves obtained are shown in FIG. 4 of the drawing. In the upper curve representing dry coal, it will be noted that a moisture dip appears at a temperature of about 140° C. and that this is followed by a large devolatilization dip at about 500° C. A typical hydrogen attack dip occurs at about 670° C. These data agree with data reported in the literature and are typical of those obtained with coal alone.

The middle curve in FIG. 4 represents the results obtained with potassium carbonate in the absence of coal. It will be noted that there was an initial moisture loss and then little change in weight until a temperature of about 800° C. was reached. A sharp dip occurred at the potassium carbonate decomposition temperature of about 890° C. Again, this curve is typical of those obtained with potassium carbonate under such conditions.

The bottom curve in FIG. 4 represents the results obtained with the Wyodak coal impregnated with potassium carbonate. It can be seen that the shape of the curve is quite different from that obtained with the dry coal and that the weight loss, beyond that due to moisture, begins at low temperature soon after heating is started. The shape of the large dip obtained with the impregnated coal at about 500° differs from that obtained with the dry coal containing no potassium carbonate. The coal and the potassium carbonate evidently react to form a coal-alkali metal salt compound or complex. Carbon dioxide is liberated from this compound or complex at a temperature well below the potassium carbonate decomposition temperature to form a carbon-alkali metal compound or complex. It is apparently this compound or complex which is responsible for the surprising methanation activity of the catalysts employed for purposes of the invention. Results similar to those shown above have been obtained by impregnating coal char and coke in lieu of coal.

EXAMPLE 2

A catalyst similar to that described in Example 1 was prepared by impregnating coal char with 20% potassium carbonate and drying the resulting material. This catalyst was then charged into a presulfided reactor and a gas containing 70% hydrogen and 30% carbon monoxide was fed to the reactor. The reactor was maintained at a temperature of 1160° F. and at a pressure of 800 psig. A feed rate of 13 liters of hydrogen per hour was employed. The product gas obtained from the reactor contained 20.10% hydrogen by volume, 3.30% carbon monoxide, 57.62% methane and 18.97% carbon dioxide. The principal reaction taking place was evidently as follows:

$$2CO + 2H_2 \rightleftharpoons CH_4 + CO_2.$$

The partial pressure ratio for the product gas for this reaction was calculated and found to be 1.96. The reaction equilibrium constant $K_{eq}$ is 1.69, indicating that the product gas composition was in equilibrium and confirming that the above reaction took place. It can thus be seen that the carbon-alkali metal catalysts promote the methanation of carbon monoxide by hydrogen and result in an equilibrium gas composition having a surprisingly high methane content.

EXAMPLE 3

Figure 5:
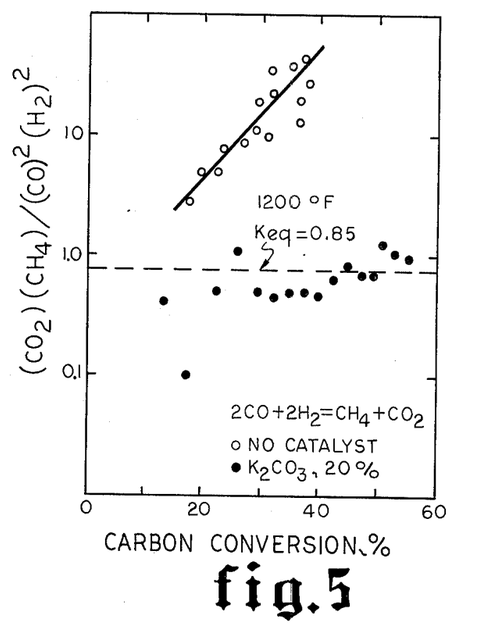
FIG. 5 is a plot showing the effect of the catalyst of the invention upon the methanation of carbon monoxide.

FIG. 5 in the drawing depicts the results obtained in a series of tests carried out in a bench scale gasification unit at 1200° F., both with and without the carbon-alkali metal catalyst containing 20% potassium carbonate. It will be noted that, in the runs carried out without the catalyst, the amount of carbon dioxide and methane increased with increasing carbon conversion. This demonstrates that the methanation reaction is not in equilibrium in the absence of the catalyst and indicates that only limited yields of methane can be obtained with such a system. In the runs carried out with the carbon-alkali metal catalyst, on the other hand, the data show that the system was substantially in equilibrium regardless of the amount of carbon conversion. By controlling the reaction conditions to favor the production of methane and carbon dioxide from hydrogen and carbon monoxide, much higher yields of methane can thus be obtained than would be possible in the absence of the catalyst.

EXAMPLE 4

Figure 6:
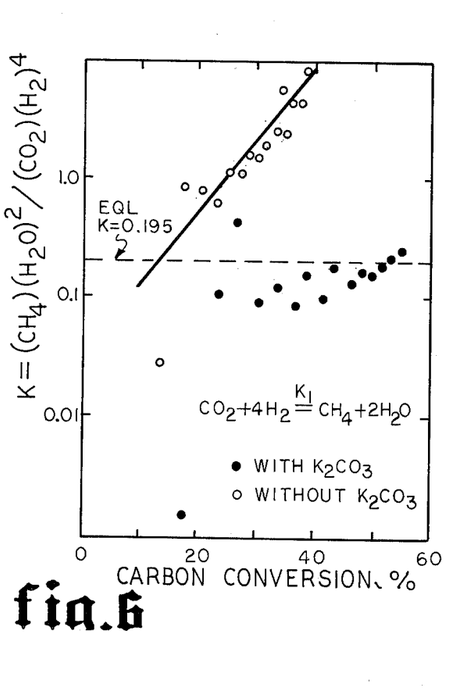
FIG. 6 is a similar plot showing the effect of the catalyst on the methanation of carbon dioxide.

FIG. 6 in the drawing is an equilibrium diagram similar to FIG. 5 for the reaction : $CO_2 + 4H_2 \rightleftharpoons CH_4 + 2H_2O$. The data shown were obtained in runs made in the bench gasification unit, with and without the carbon-alkali metal catalyst. Again it will be noted that the reaction carried out in the absence of the catalyst was not in equilibrium. The data demonstrate that, in the presence of the catalyst, the reaction was in equilibrium and that the catalyst can thus be used effectively to promote the methanation of carbon dioxide to form methane gas.

EXAMPLE 5

Figure 7:
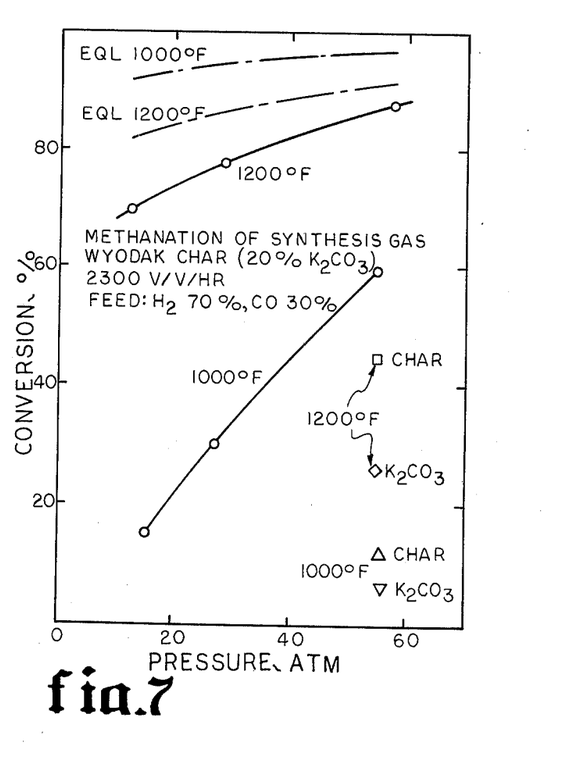
FIG. 7 is a plot illustrating the methanation of synthesis gas containing 70% hydrogen and 30% carbon monoxide in the presence of a carbon-alkali metal catalyst and in the absence of such a catalyst.

In a further series of experimental runs, a synthesis gas containing 30% carbon monoxide and 70% hydrogen was methanated in a bench scale reactor at temperatures of 1000 and 1200° F. and at pressures of about 15, 25 and 55 atmospheres, both in the presence and in the absence of the carbon-alkali metal catalysts. The catalyst used was prepared by impregnating Wyodak char with 20% potassium carbonate, drying the treated char, and then heating the dried material to the methanation reaction temperature. For purposes of comparison, runs were made at 55 atmospheres and at 1000° F. and 1200° F. in the presence of char alone and in the presence of potassium carbonate alone. The data of of FIG. 7 show that, in the presence of carbon-alkali metal catalyst, the conversion obtained increased rapidly with increasing pressure and that at 1200° F. conversions in excess of about 80% were obtained. The equilibrium curves for the reaction at 1000° F. and at 1200° F. are shown on the drawing for purposes of comparison. It will be noted that the runs made in the presence of char alone and in the presence of potassium carbonate alone resulted in much lower conversion values than those obtained in the presence of the catalyst. It is particularly interesting to note that the conversion values with potassium carbonate alone were lower than those obtained with char alone. This clearly demonstrates that char and potassium carbonate individually have little catalytic effect upon the methanation reaction and that both constituents of the carbon-alkali metal catalysts are necessary to effectively catalyze the methanation of carbon monoxide and carbon dioxide.

EXAMPLE 6

Figure 8:
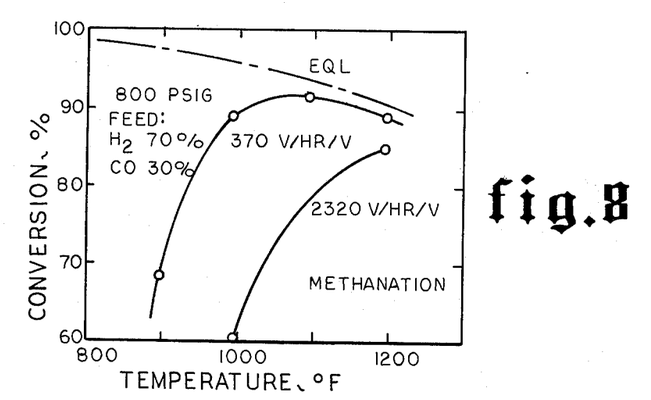
FIG. 8 is a plot illustrating the effect of temperature on the methanation of synthesis gas in the presence of a carbon-alkali metal catalyst.

The effect of temperature on the methanation of carbon monoxide in the presence of the carbon-alkali metal catalysts is shown in FIG. 8 of the drawing. The runs depicted in FIG. 8 were carried out with a feed gas containing 70% hydrogen and 30% carbon monoxide at a pressure of 800 psig and at two different feed rates. One set of runs was carried out at 370 volumes of gas per hour per volume of carbon-alkali metal catalyst and the other runs were made at 2320 volumes per hour per volume of the catalyst. The catalyst used in both sets of runs was prepared by impregnating coal char with 20% by weight of potassium carbonate, drying the impregnated char, and then heating the treated material to a temperature of about 900° F. or higher. The equilibrium curve for the methanation reaction is depicted in FIG. 8. It can be seen that the runs carried out at 370 v/hr/v gave increasing conversion values with increasing temperatures up to a temperature of about 1100° F. As might be expected from the equilibrium curve for the reaction, the run made at 1200° F. gave a lower conversion value than that at 1100° F. The runs made at the higher feed rate gave a conversion rate-temperature curve similar to that obtained at the lower feed rate. If a temperature above 1200° F. had been used at the higher feed rate, the equilibrium curve indicates that a somewhat lower conversion rate would probably have been obtained. Although somewhat higher temperatures can be used, it is preferred to carry out the final stage of the methanation reaction at relatively low temperatures between about 900° and about 1200° F.

EXAMPLE 7

Figure 9:
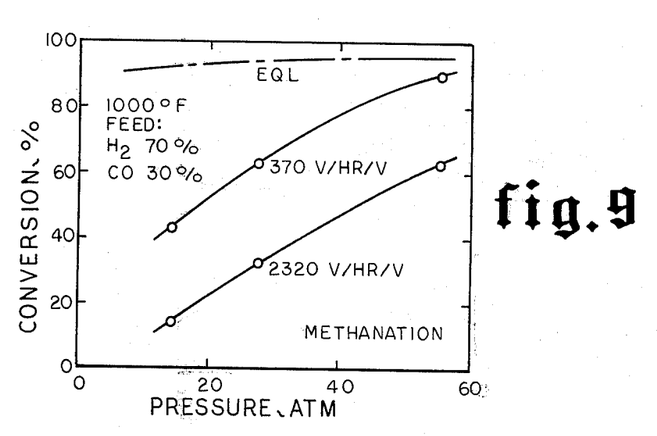
FIG. 9 is a plot showing the effect of pressure on the methanation of synthesis gas in the presence of a carbon-alkali metal catalyst.

FIG. 9 in the drawing illustrates the effect of pressure on the methanation reaction. The two curves in FIG. 9 representing runs made at 370 v/hr/v and 230 v/hr/v show that the percent conversion increased rapidly as the pressure was increased from 15 atmospheres to about 55 atmospheres for the reaction at 1000° F. The conversions obtained at the higher feed rate were lower than those at 370 v/hr/v. At the lower feed rate, the conversion at 55 atmospheres was about 90% and was only slightly less than that indicated by the equilibrium curve for the reaction.

EXAMPLE 8

Figure 10:
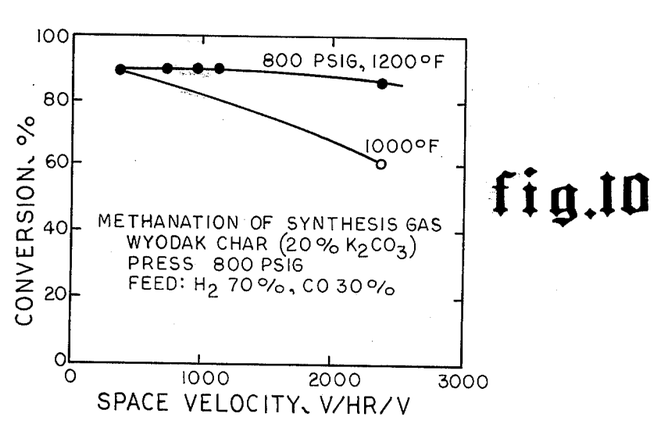
FIG. 10 is a plot showing the effect of variations in space velocity on the methanation of synthesis gas in the presence of a carbon-alkali metal catalyst.

FIG. 10 is a plot showing the effect of variations in space velocity on the conversion obtained at 800 psig and 1200° F. in the presence of a carbon-alkali metal catalyst prepared from Wyodak char and 20 weight percent potassium carbonate. One run at a temperature of 1000° F. is also shown. The data indicate that at 800 psig and 1200° F. variations in the space velocity had relatively little effect upon the amount of conversion obtained. At the 1200° F. temperature, the conversion values are close to those indicated by the equilibrium curve for the reaction and hence the effect of variations in the feed rate is small. At lower temperatures, however, an increase in the space velocity produces a decrease in the amount of conversion obtained and this is shown by the curve representing runs at 1000° F.

EXAMPLE 9

In a further series of experiments, a catalyst ws prepared by impregnating dry coal char particles between 30 and 80 mesh on the U.S. Sieve Series Scale with an aqueous solution of cesium carbonate until about 20% by weight of the cesium carbonate had been deposited. The particles were then dried in an oven overnight. The resulting catalyst was charged to an electrically heated stainless steel reactor and a synthesis gas containing 70 volume percent hydrogen and 30 volume percent carbon monoxide was fed to the top of the reactor above the fixed catalyst bed. The pressure in the reactor was controlled by means of a back pressure regulator at 1000 psig and the product gas withdrawn from the bottom of the unit was fed to a water-cooled condenser, two gas chromatographs in series, and finally a wet test meter. Both the catalyst and reactor were presulfided by passing hydrogen sulfide into the system during the reactor heat up period. Runs were carried out at temperatures of from 1000 to 1200° F. and at a space velocity of 1600 v/hr/v.

Figure 11:
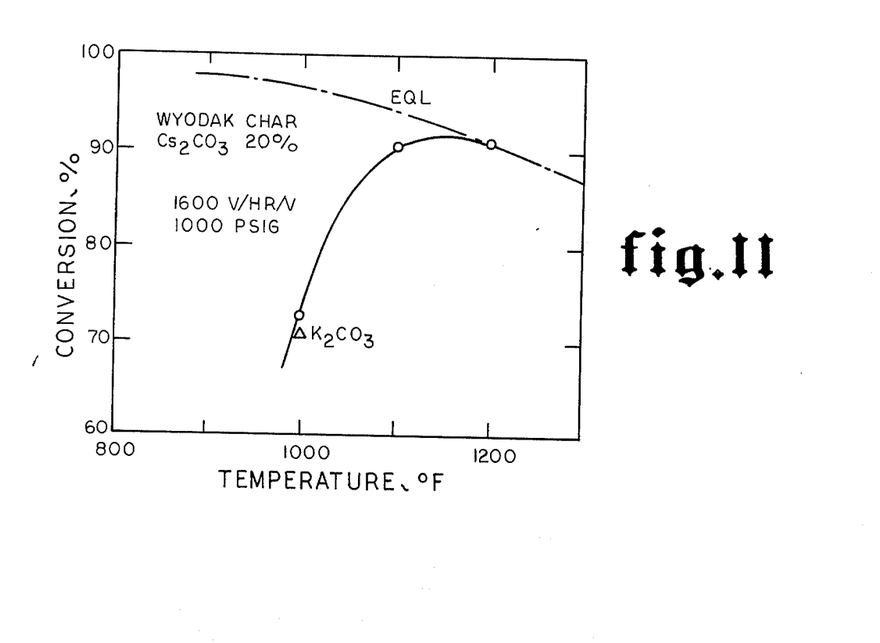
FIG. 11 is a plot illustrating the methanation of a mixture of carbon monoxide and hydrogen in the presence of cesium carbonate and potassium carbonate on coal char.

The results of the runs referred to above are shown in FIG. 11 of the drawing. It was found that the catalytic activity of the catalyst prepared from cesium carbonate and coal char was about the same, at temperatures of 1100° and 1200° F., as that of similar catalysts prepared with potassium carbonate and coal char. At 1000° F., however, the catalyst prepared with the cesium carbonate was slightly better than that prepared with the potassium carbonate. The conversion value obtained with the carbonpotassium carbonate catalyst at 1000° F. is shown in FIG. 11 to illustrate this. For lower temperatures, it may therefore be advantageous to employ cesium compounds for preparing the catalysts even though such compounds are ordinarily more expensive than the corresponding potassium compounds.

EXAMPLE 10

Additional runs similar to those described above were carried out using a series of alkali metal catalysts prepared from various potassium compounds. These runs were conducted at a temperature of 1200° F., a pressure of 800 psig, and at space velocities between about 400 and about 2400 v/hr/v. The catalysts tested were prepared from Wyodak coal char and potassium carbonate, potassium hydroxide, potassium sulfate, and potassium chloride. In each case 20% of the potassium compound by weight was used. The results obtained are shown in FIG. 12 of the drawing.

Figure 12:
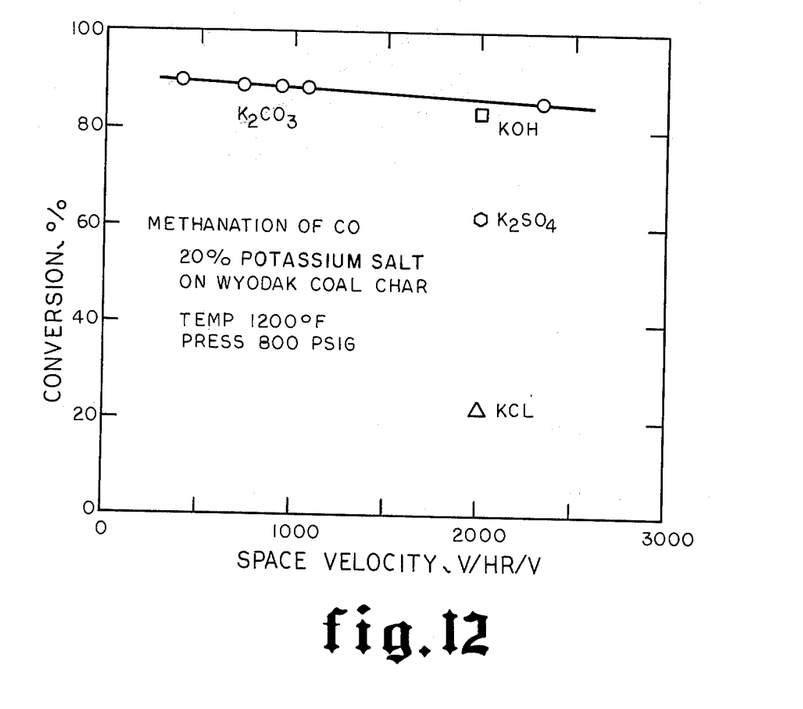
FIG. 12 shows the effect of other alkali metal compounds on the methanation of carbon monoxide and hydrogen.

It will be noted from FIG. 12 that the catalysts prepared from potassium carbonate and potassium hydroxide gave generally similar results. The conversion level of the feed gas with the catalyst prepared with potassium sulfate was initially about 55% but gradually increased to about 70% after 24 hours running time. The catalyst prepared from potassium chloride gave poor results under the conditions employed but may be somewhat more effective under other operating conditions.

It will be apparent from the foregoing that the invention provides an improved methanation process carried out with catalysts which have pronounced advantages over methanation catalysts employed in the past. Although the process has been described in connecton with a particular gasification process and in terms of a particular type of methanation reactor, it will be understood that mixtures of hydrogen and carbon oxides from a variety of different sources can be methanated using the improved catalysts and that the process is not restricted to the particular flow plan shown in the drawing.

We claim:

1. A method for the production of a methane-rich gas which comprises introducing a gaseous mixture of hydrogen and at least one carbon oxide into a reaction zone containing a carbon-alkali metal catalyst at a temperature between about 800° F. and about 1500° F. and at a pressure between about atmospheric and about 2000 psig, said catalyst being prepared by heating an intimate mixture consisting essentially of a carbonaceous solid and an alkali metal constituent to an elevated temperature sufficient to produce a reaction between the carbon and alkali metal in said mixture and form a carbon-alkali metal reaction product, and recovering a methane-rich gas from said reaction zone.

2. A method as defined by claim 1 wherein said gaseous mixture is a raw synthesis gas produced by the steam gasification of a carbonaceous feed material.

3. A method as defined by claim 1 wherein said carbonaceous solid is coal.

4. A method as defined by claim 1 wherein said carbonaceous solid is coal char.

5. A method as defined by claim 1 wherein said alkali metal constituent is a potassium compound.

6. A method as defined by claim 1 wherein said alkali metal constituent is a cesium compound.

7. A method as defined by claim 1 wherein said carbon oxide is carbon monoxide.

8. A method as defined by claim 1 wherein said intimate mixture of said carbonaceous solid and said alkali metal constituent is prepared by impregnating said solid with a liquid containing an alkali metal compound soluble in said liquid.

9. A process for the production of a methane-rich gas which comprises reacting steam with a carbonaceous feed material to produce a synthesis gas containing hydrogen and carbon monoxide; contacting said hydrogen and carbon monoxide with a carbon-alkali metal catalyst prepared by impregnating finely-divided carbonaceous solids with a solution consisting essentially of an alkali metal compound and an aqueous carrier and heating the impregnated solids at an elevated temperature sufficient to produce a carbon-alkali metal reaction product in the impregnated solids, said gas being contacted with said catalyst at a temperature in the range between about 800° F. and about 1500° F. and at a pressure between about atmospheric and about 2000 psig; and recovering a gas of enhanced methane content.

10. A process as defined by claim 9 wherein said carbonaceous feed material is coal.

11. A process as defined by claim 9 wherein said carbonaceous solids comprise coal char and said alkali metal compound is a cesium compound.

12. A process as defined by claim 9 wherein said alkali metal compound is a potassium salt of an acid having an ionization constant less than $1 \times 10^{-3}$.

13. A process as defined by claim 9 wherein said alkali metal compound is a hydroxide.

14. A process as defined by claim 9 wherein said alkali metal compound is a carbonate.

15. A process as defined by claim 9 wherein said alkali metal compound is a sulfate.

16. A process as defined by claim 9 wherein said hydrogen and carbon monoxide are contacted with said catalyst at a temperature between about 900° and about 1350° F. and at a pressure between about 100 and about 250 psig.

17. A process as defined by claim 9 wherein said steam is reacted with said carbonaceous feed material in the presence of an alkali metal compound.

18. A process as defined by claim 9 wherein said hydrogen and carbon monoxide are contacted with said catalyst in staged reactors and the gas is cooled between stages.

* * * * *